United States Patent [19]

Shoesmith

[11] Plant 4,400

[45] Mar. 27, 1979

[54] CHRYSANTHEMUM NAMED CONSTITUTION

[75] Inventor: Leonard H. Shoesmith, Westfield-Woking, England

[73] Assignee: Pan-American Plant Company, West Chicago, Ill.

[21] Appl. No.: 783,011

[22] Filed: Mar. 30, 1977

[51] Int. Cl.[2] ..... A01H 5/00

[52] U.S. Cl. ..... Plt./78

[58] Field of Search ..... Plt./78

*Primary Examiner*—Robert E. Bagwill
*Assistant Examiner*—James R. Feyrer
*Attorney, Agent, or Firm*—Chas. W. Rummler

[57] ABSTRACT

A new variety of chrysanthemum plant for cut flower production characterized by the large size of its clear yellow flowers which are borne singly on long peduncles carried as a spray on tall strong canes. This plant has a tall, upright growth habit with strong, erect stems, and a good tolerance to high soluble salt conditions.

1 Drawing Figure

BACKGROUND OF THE NEW PLANT

My new chrysanthemum plant originated as a seedling of unidentified parentage and was discovered by me in 1972 among plants growing in my greenhouse at Westfield-Woking, Surrey, England, and maintained as breeding stock for my breeding efforts seeking new and improved chrysanthemum varieties for the commercial market. This new plant caught my attention because of its height and the relatively long stems which carried large, lovely, yellow blooms of a kind suitable for use as cut flowers.

Asexual propagation of this new plant by cuttings from the original plant, and further asexual propagation of this variety through successive generations, carried on by me at Westfield-Woking, Surrey, England, has demonstrated conclusively that the distinctive characteristics of the original plant are faithfully carried from generation to generation and are firmly fixed. Commercial scale propagation of this new variety of chrysanthemum is now being done at West Chicago, Ill., and at Cortez, Fla., with full retention of the distinctive qualities of my original discovery.

DESCRIPTION OF THE DRAWINGS

My new chrysanthemum discovery is illustrated by the accompanying drawings, the first of which is a full color photographic view showing the new plant with buds, foliage and fully opened blossoms, and the second drawing is a printed reproduction of a machine made photoprint of typical specimens of the leaves taken from various locations on a flowering stem. The colors shown in the photographic drawing are believed to be as closely true as it is reasonably possible to obtain through conventional photographic procedures. The average color for midyear blooming (RHS 6A) is shown by the painted patch affixed to the drawing below the photographic view.

DESCRIPTION OF THE NEW PLANT

The following is a detailed description of my new chrysanthemum plant based upon observations of greenhouse grown plants made in 1976 at West Chicago, Ill., the color designations being according to the R.H.S. Colour Chart published by The Royal Horticultural Society of London, England, with the collaboration of The British Colour Council.

THE PLANT

Origin: Seedling.
Parentage: Both seed parent and pollen parent are unidentified chrysanthemum varieties.
Classification:
*Botanic.*—*Chrysanthemum morifolium.*
*Commercial.*—Greenhouse pot plant.
Form: Tall herbaceous bush.
Height: 2 to 4 feet.
Growth: Vigorous and upright, sturdy and with very good strength.
Branching: Normal.
Foliage: Abundant with 3 to 5 leaves per 6 inches of stem.
*Leaf Size.*—$3\frac{3}{4}$ to $5\frac{1}{2}$ inches long and 2 to $3\frac{5}{8}$ inches wide.
*Leaf Shape.*—Lobed-lanceolate with slightly serrated margins.
*Surface Aspect.*—Candescent.
*Color.*—Upper side — RHS 147A. Under side — RHS 147B.
*Venation.*—Pinnately veined.
*Petioles.*—$\frac{5}{8}$ to $1\frac{1}{4}$ inches long.

THE BUD

Form: Globular.
Size:
*Diameter.*—$\frac{3}{8}$ to 9/16 inch.
*Depth.*—$\frac{1}{4}$ to $\frac{3}{8}$ inch.
Opening rate: Slow.
Color:
*When phyllaries first divide.*—RHS 144A, 145A, 154A depending upon flowering season.
*When florets begin to unfurl.*—RHS 7A.
Phyllaries: The outside of the receptacle bears many involucral spear-shaped and upstanding bracts.
Color:
*Inside.*—RHS 137A.
*Outside.*—RHS 137B.
Surface aspect: Pubescent.
Peduncle: Erect and $2\frac{1}{4}$ to 6 inches long.
Surface aspect: Pubescent.

THE FLOWER

Response: 9-week.
Recommended flowering: The year around.

Natural flowering season: October 25 to November 2.

Blooms: Flower type — Composite and decorative.

*Borne.*—A head of many florets borne on a receptacle.

*Size.*—Large. Diameter — 2¾ to 3⅜ inches. Depth — ⅞ to 1⅝ inches.

*Shape.*—Flat when bloom first opens, the outer petals reflexing slightly as bloom matures.

*Florets.*—Numerous in number.

*Form.*—Linear with obtuse apex.

| Color: (RHS) Flower Season: | Jan. | Apr. | May | June | Aug. | Oct. |
|---|---|---|---|---|---|---|
| Outer Florets: | | | | | | |
| Upper side — | 9A | 9B | 6A | 5A | 6B | 6A,B 7B,C |
| Reverse side — | 7B | 7C | 6C | 5C | 6C | 6C, 7D 8B |
| Inside Florets: | | | | | | |
| Upper side — | 9A | 9B | 6A | 5A | 12A | 9A,B |
| Reverse side — | 7A | 9B | 12A | 9B | 12B | 7B,C |
| Tonality at a distance of 6 feet — 6A | | | | | | |

*Appearance.*—Very slightly shiny.

*Discoloration.*—Very slight fade after full bloom.

Peduncle: Sturdy and upright.

*Length.*—2¼ to 6 inches.

*Color.*—RHS 147B.

Persistence: Florets hang on and dry.

Lasting quality:

*On the plant.*—3 weeks.

*As a cut flower.*—7 to 16 days.

REPRODUCTIVE ORGANS

Stamens:

*Arrangement.*—5 syngenesious stamens.

*Filaments.*—Length — 1-1/16 to 1⅛ inch.

*Color.*—Light yellow.

*Pollen.*—Yellow.

Pistils:

*Number.*—One to each ray and disc floret.

*Styles.*—⅛ to 3/16 inch long.

*Stigmas.*—Color — Yellow.

Ovaries: Inferior bicarpellate.

This new chrysanthemum cultivar is particularly distinguished by the large size and decorative flower form of its blooms, its tall plant height and vigorous upright growth habit, the long lasting quality of its blooms, on the plant and as cut flowers, and its tolerance to high soluble salt conditions.

This variety has flowers with a clear yellow color in the ray florets when flowered under warm temperatures and with some bronze streaking which causes a deepening or darkening of the blossom colors when flowered under cool temperatures. The plant has a 9-week response in summertime and a 10-week wintertime response.

I claim

1. The new and distinctive chrysanthemum cultivar, substantially as herein shown and described, characterized by its tall and vigorous growth with strong erect stems bearing large yellow flowers having relatively long peduncles.

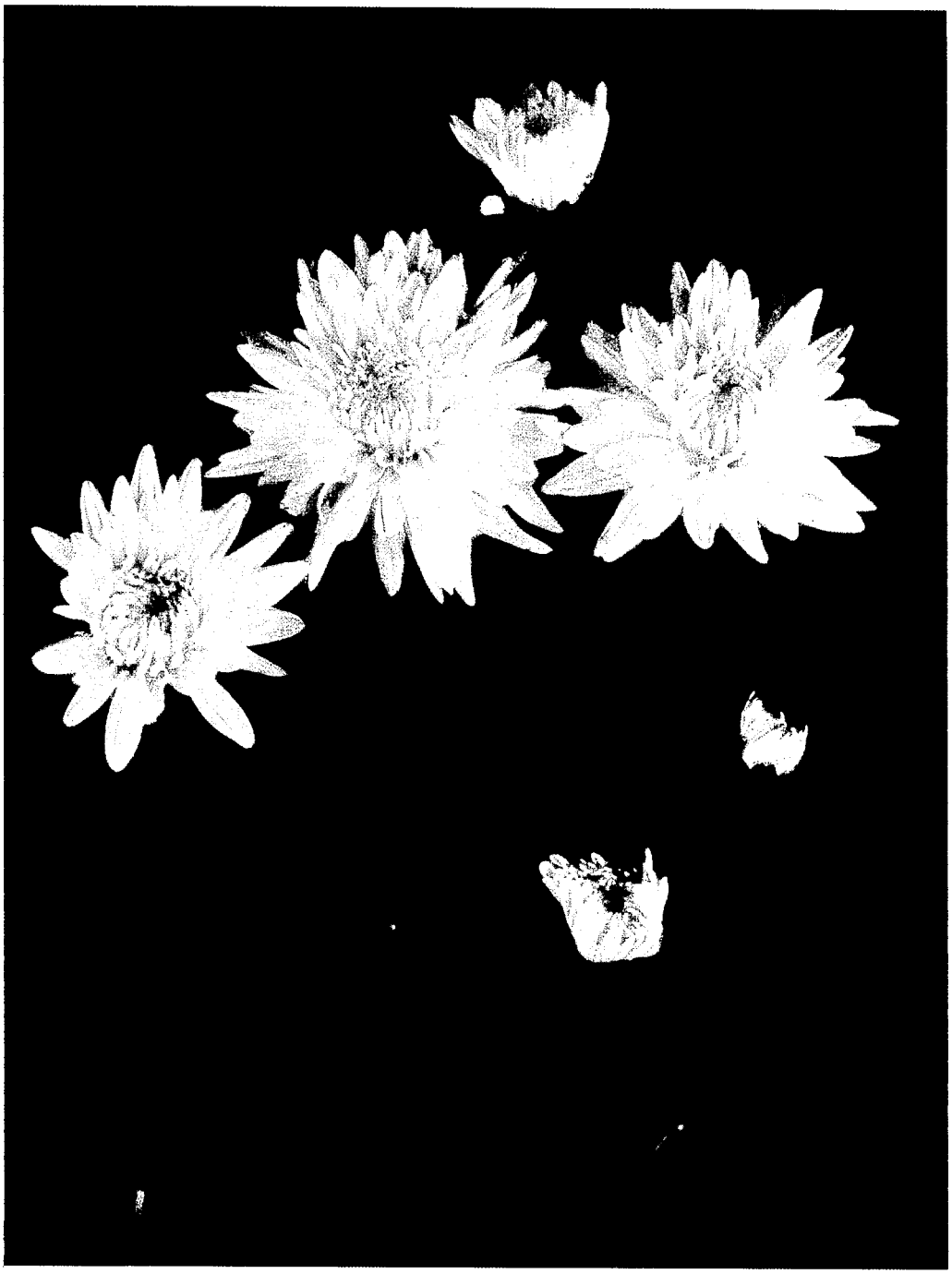

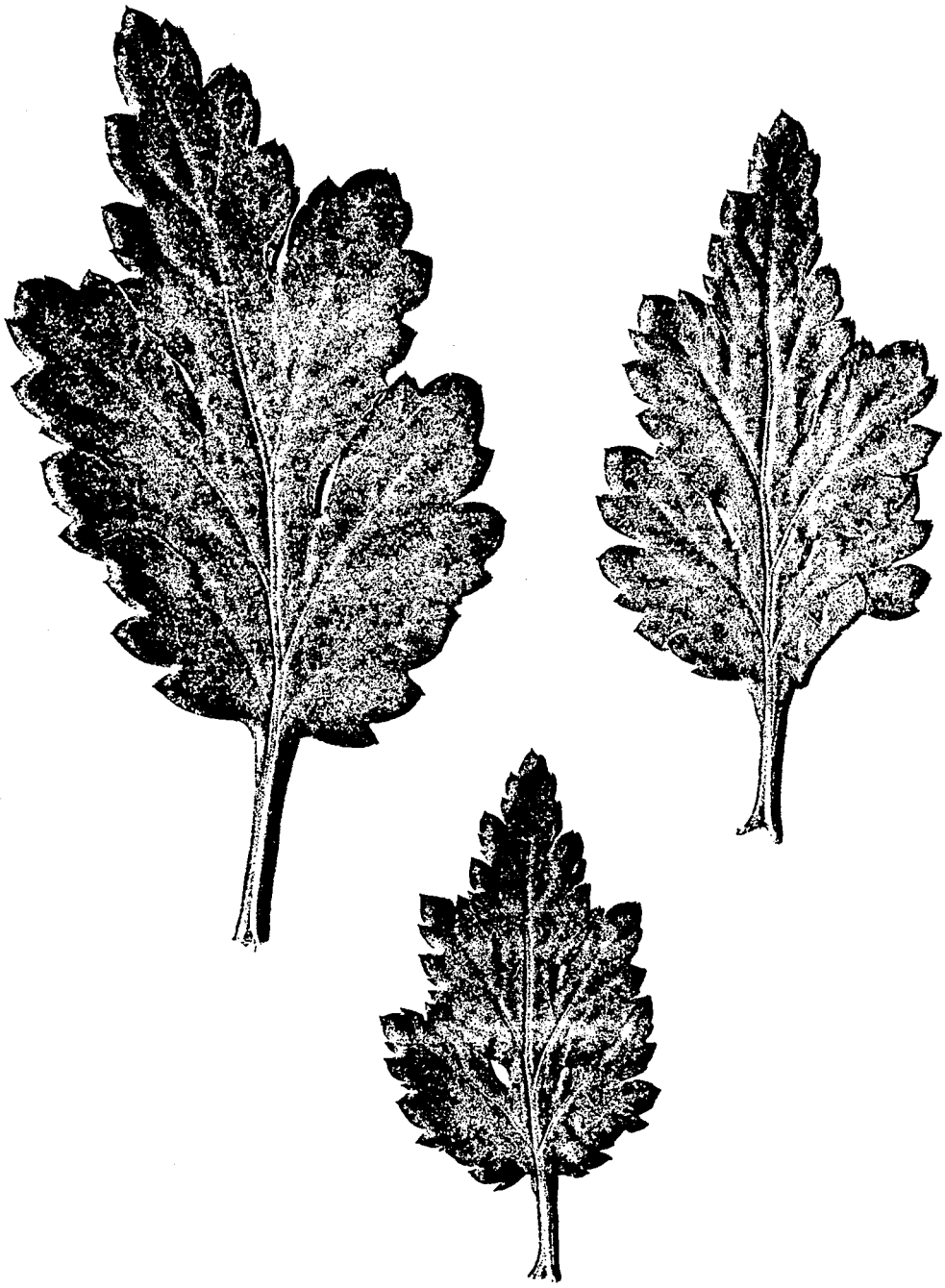

* * * * *